United States Patent [19]

Carlson et al.

[11] 4,256,114
[45] Mar. 17, 1981

[54] REFRACTORY MEASUREMENT CIRCUITRY

[75] Inventors: Scott W. Carlson, Blaine; James T. Bartelt, Shoreview, both of Minn.

[73] Assignee: Cardiac Pacemakers, Inc., St. Paul, Minn.

[21] Appl. No.: 87,791

[22] Filed: Oct. 24, 1979

[51] Int. Cl.$^3$ .............................................. A61N 1/36
[52] U.S. Cl. ............................................. 128/419 PT
[58] Field of Search .................... 128/419 PT, 419 PG

[56] References Cited

U.S. PATENT DOCUMENTS

| 3,921,642 | 11/1975 | Preston et al. | 128/419 PG |
| 4,021,736 | 5/1977 | Walters et al. | 128/419 PT |
| 4,173,230 | 11/1979 | Digby | 128/419 PG |

*Primary Examiner*—William E. Kamm
*Attorney, Agent, or Firm*—Haugen, Orrin M.; Thomas J. Nikolai

[57] ABSTRACT

An electronic test instrument for measuring the refractory interval of a demand-type cardiac pacer pulse generator. The normal pulse-to-pulse interval of the pacer under test is measured by accumulating regularly occurring timing signals in a first counter during the interpulse period. At a predetermined time after the occurrence of the first pulse defining the interval, a pseudo R-wave is generated and applied to the pacer under test. The next pulse-to-pulse interval is then measured in a second counter in a fashion similar to the first measurement and a test is made to determine if the second interval exceeds the first by a prescribed amount. If so, it is known that the pseudo R-wave was effective to reset the pacer's pulse generator. If not, the time of occurrence of the next pseudo R-wave is delayed by a further known amount and the operation is repeated over and over until an extension of the normal pulse-to-pulse interval is noted. When a point is reached where the pseudo R-wave is displaced in time from a first pacer pulse just enough to cause resetting of the pacer's pulse generator, a measure is made of the displacement interval and this value is visually displayed.

9 Claims, 7 Drawing Figures

REFRACTORY MEASUREMENT CIRCUITRY

I. Field of the Invention

This invention relates to electronic test equipment, and more specifically to a hand-held, portable, battery-powered test instrument for evaluating the performance characteristics of a demand-type cardiac pacer pulse generator, particularly the refractory interval of that pacer.

II. Discussion of the Prior Art

As is well known in the art, a demand-type pacer is one that is capable of sensing normal heart activity and of having its timing circuitry associated with the generation of artificial stimulating impulses reset when natural R-waves are regularly detected, such that the pulse generator is precluded from issuing pacer pulses. In the absence of normal R-wave activity in the heart, however, the timer circuitry in the pacer is allowed to run its course and issue a pacer pulse at regular intervals until natural R-wave activity is again detected.

Prior art demand-type pacer pulse generators also include an additional timing circuit for establishing what is known as the refractory period. It is known that following the occurrence of a natural heart beat or an artificially stimulated heart beat, the heart organ is effectively inhibited from responding to further stimulation until a predetermined time period has elapsed. This period is normally referred to as the refractory interval. So that a cardiac pacer pulse generator will operate somewhat in synchrony with the heart, such circuits often include a feature whereby the R-wave sensing circuitry remains unresponsive to electrical signals picked up by the heart contacting electrodes for a predetermined time period after a pacing output stimulus has been applied to the heart. This time period or interval is commonly referred to as the "paced refractory period", and during this interval, the electronic circuitry is allowed to recover. In a related fashion, some prior art pacer pulse generators include a distinct interval referred to as the "sensed refractory period" which may be defined as the timespan following a sensed pulse when the pacer pulse generator is incapable of sensing any additional electrical activity.

In evaluating the performance of a cardiac pacer pulse generator, it is desirable to measure both the paced refractory period and the sensed refractory period for that pulse generator. While the Ferreira Patent 4,141,367 is concerned with a portable test instrument for evaluating the performance of cardiac pacer pulse generators, it is silent as far as any description of an ability in that instrument to measure refractory intervals. In fact, applicant is unaware of any prior art test device wherein the refractory period for a pacer pulse generator may be accurately measured and displayed to the user with the simple press of a push button.

SUMMARY OF THE INVENTION

The refractory interval measurement scheme employed utilizes digital logic throughout. The pacer to be tested is connected by leads to the test instrument of the present invention and the normal pulse-to-pulse interval for that pacer is measured by accumulating relatively high frequency, regularly occurring clock signals in a counter during the interval in question. At a predetermined time following the occurrence of the second of a series of two pacer pulses which define the interval in question, a pseudo R-wave is generated by the test apparatus and applied to the pacer under test. A further digital counter is provided for accumulating the aforementioned clock pulses during a second pulse-to-pulse interval following the occurrence of the pseudo R-wave. Following that, the count proportional to the length of the second interval is compared to that corresponding to the first interval to determine whether the pseudo R-wave had the effect of extending the normal pulse-to-pulse interval originally measured. If so, it is known that the pseudo R-wave was effective to reset the pacer's timing circuit and that it therefore occurred outside of the refractory interval of the pacer. If the second interval is not extended, however, the time of occurrence of the next pseudo R-wave is delayed by a further known increment and the operation is repeated until an extension of the normal pulse-to-pulse interval is noted. Circuitry is provided for selectively increasing or decreasing the displacement time of the pseudo R-wave with respect to the onset of a timing interval. Thus, the circuitry involved has the ability to home in upon the point where the pseudo R-wave is displaced in time from a first pacer pulse just enough to effect resetting of the pacer's pulse generator. A measure is made of this displacement interval and the value is visually displayed on a LED numeric display panel.

OBJECTS

It is accordingly the principal object of the present invention to provide a new and improved test instrument and method for facilitating the evaluation of the performance characteristics of a cardiac pacer pulse generator.

Another object of the invention is to provide in a hand-held, portable, battery powered electronic test instrument the ability to accurately measure the refractory period of a demand-type pacer pulse generator.

Still another object of the invention, related to the immediately foregoing object, is to provide a test instrument of the type described which may be used to measure both paced refractory periods and sensed refractory periods.

A still further object of the invention is to provide a circuit comprised of interconnected, commercially available digital logic devices which is capable of accurately measuring to a desired degree of accuracy the length of the refractory period(s) of a demand-type cardiac pacer pulse generator.

These and other objects and advantages of the invention will become apparent to those skilled in the art from the following detailed description of the preferred embodiment, especially when considered in conjunction with the accompanying drawings.

DESCRIPTION OF THE PREFERRED EMBODIMENT

Figure 1:
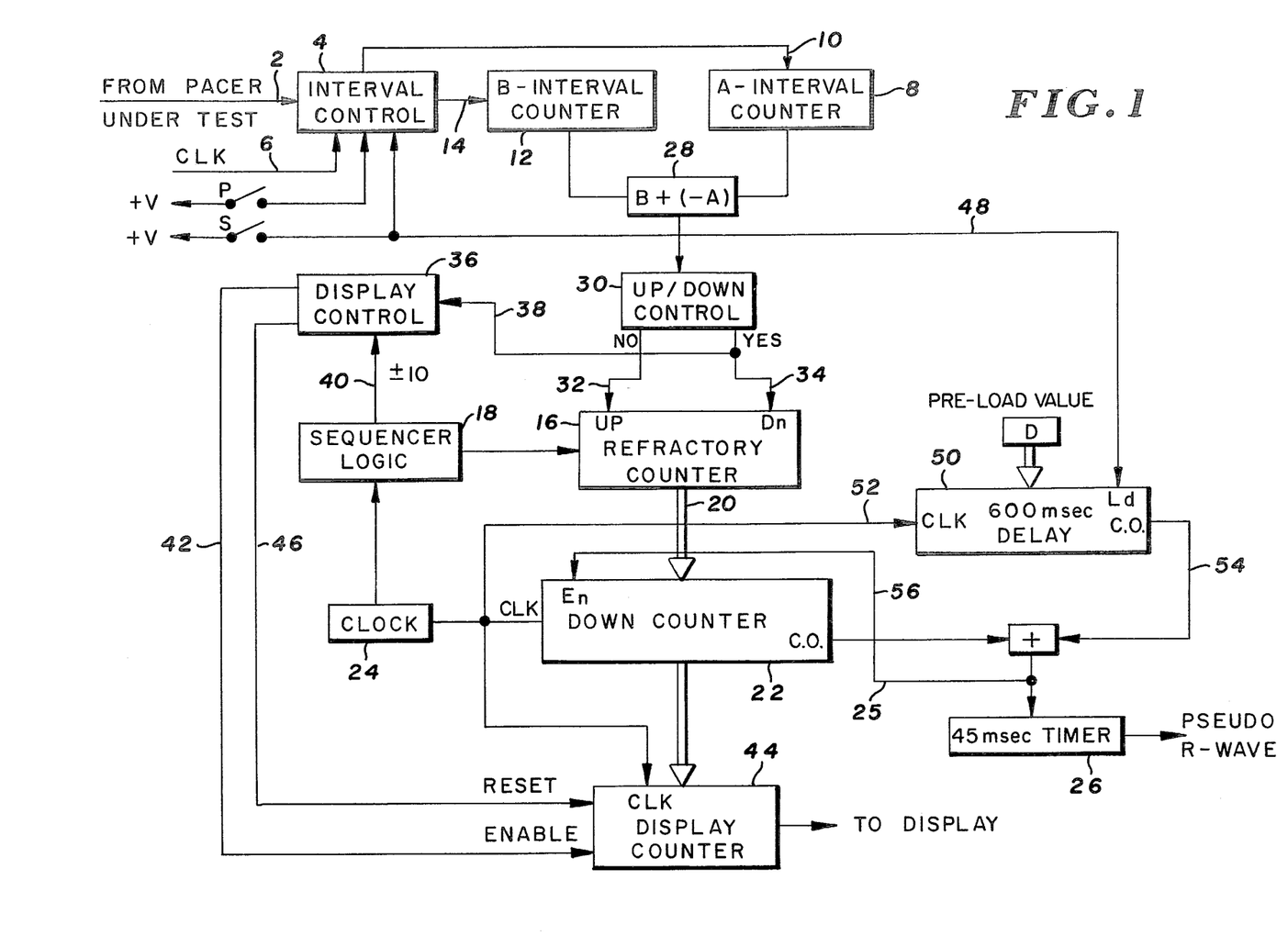
FIG. 1 is a general block diagram showing the logical organization of the test apparatus of the present invention.
Figure 3:
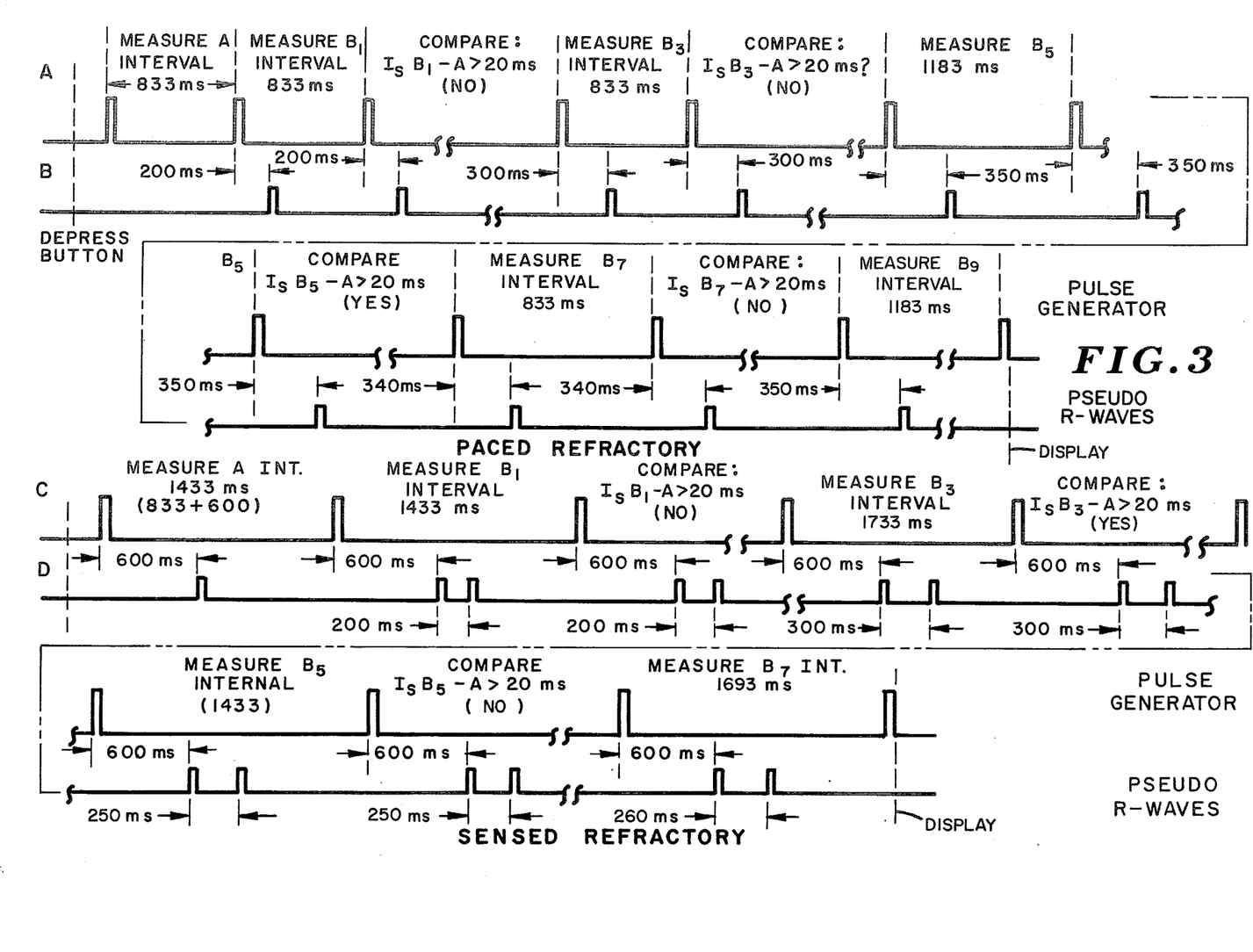
FIG. 3 is a timing diagram relating to the system of FIG. 1.
Figure 4:
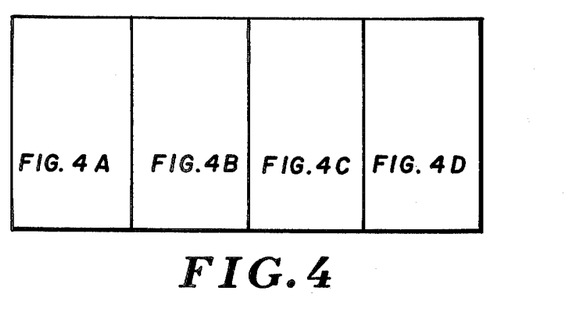
FIG. 4A through 4D, when arranged as shown in FIG. 4, sets forth by means of a logic diagram the best mode contemplated for practicing the invention.
Figure 4A:
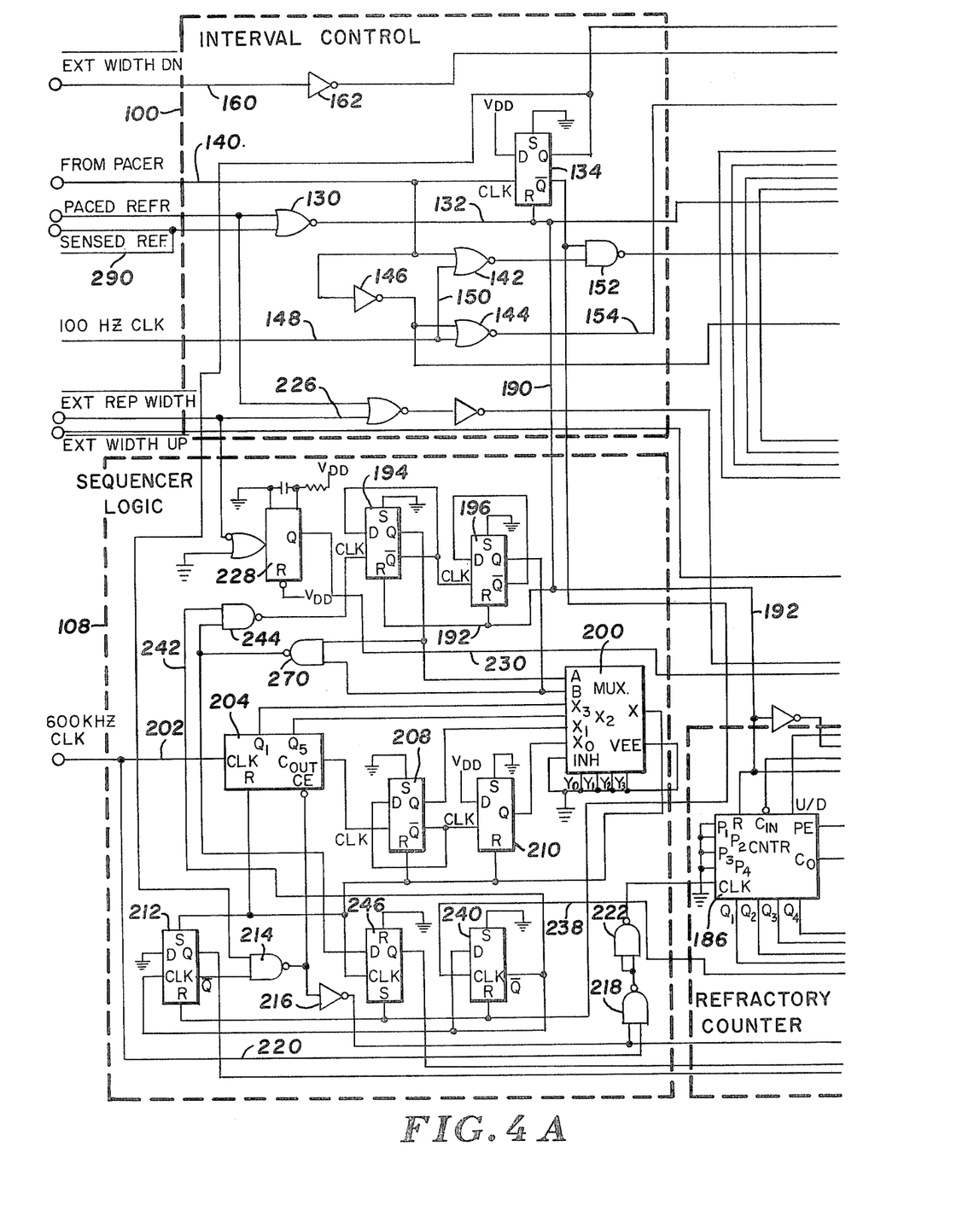
Figure 4B:
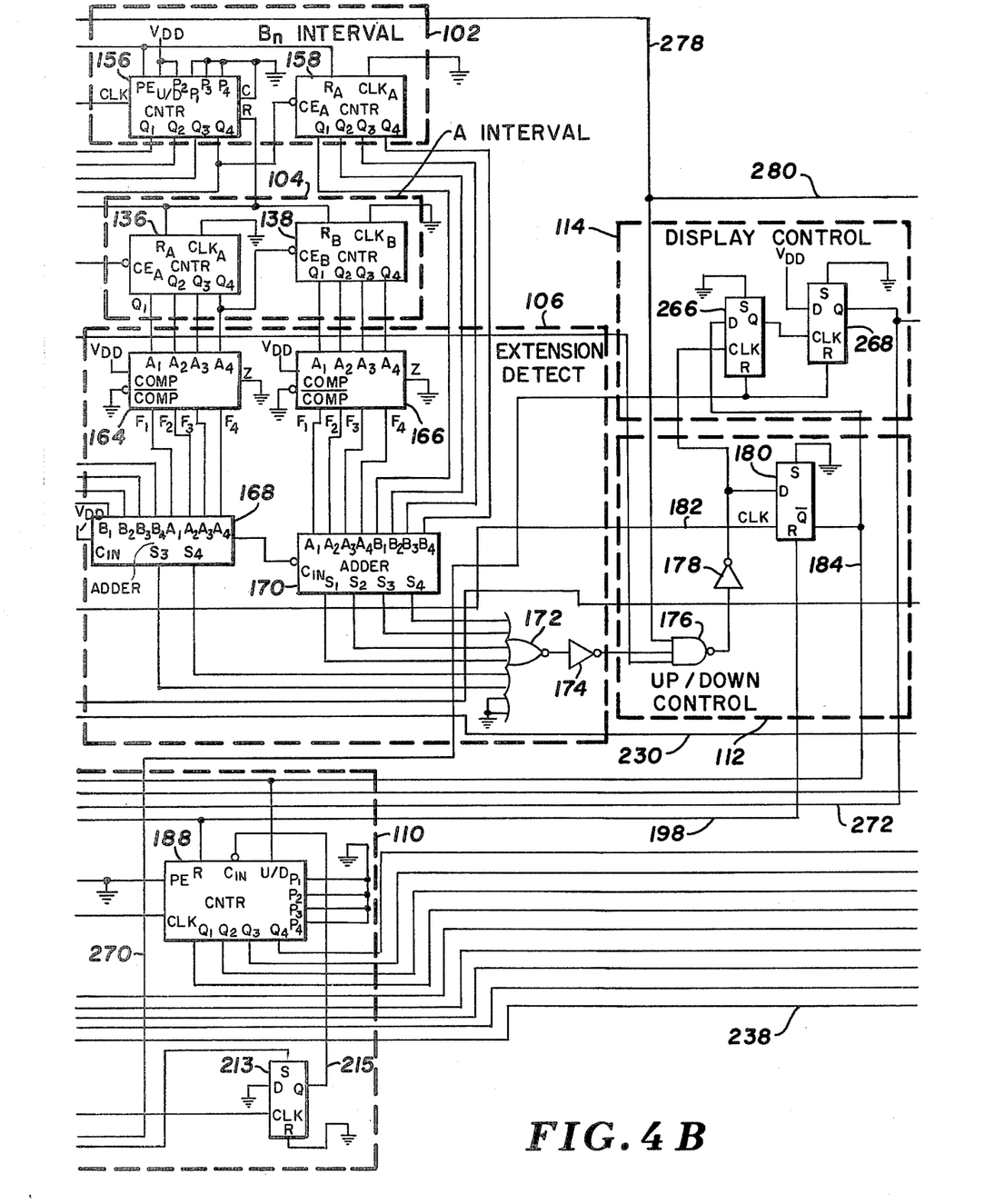
Figure 4C:
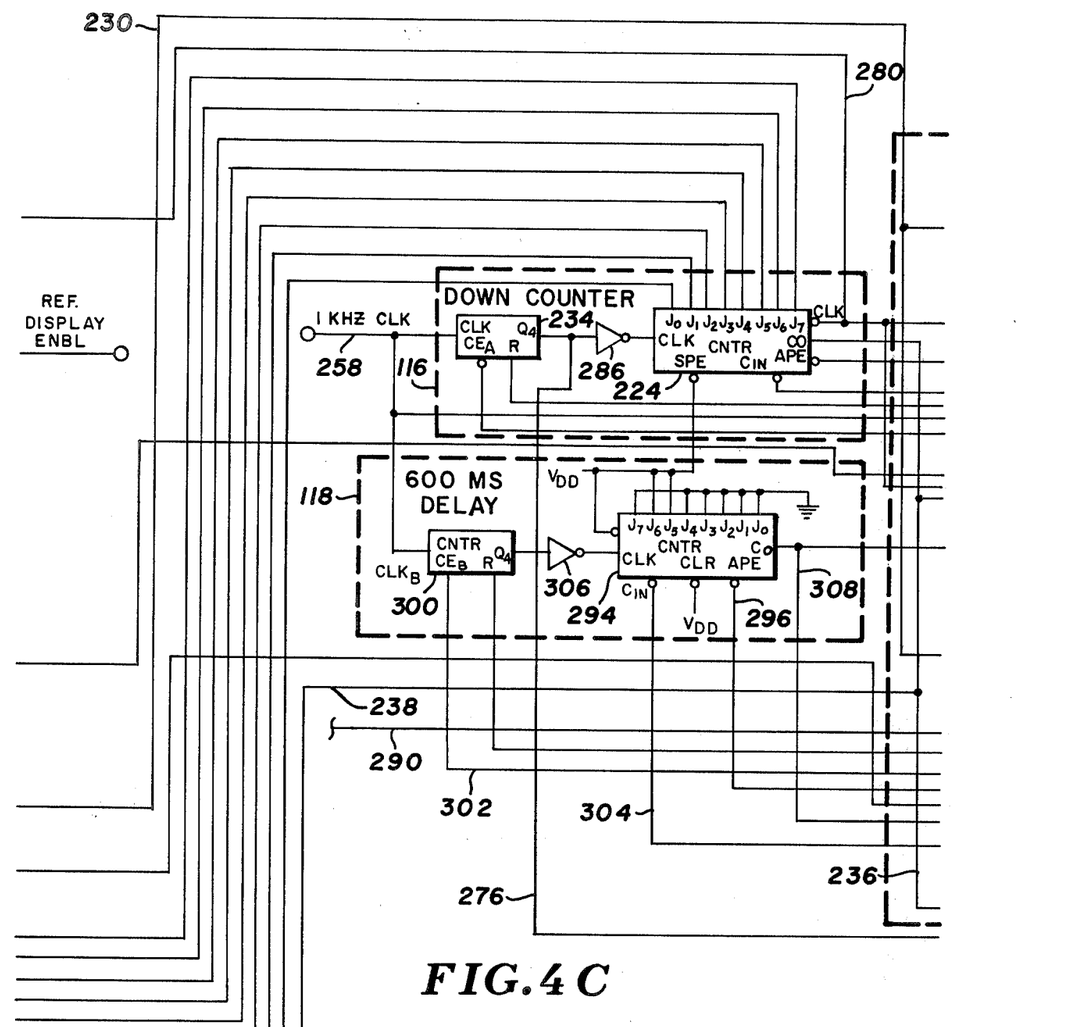
Figure 4D:
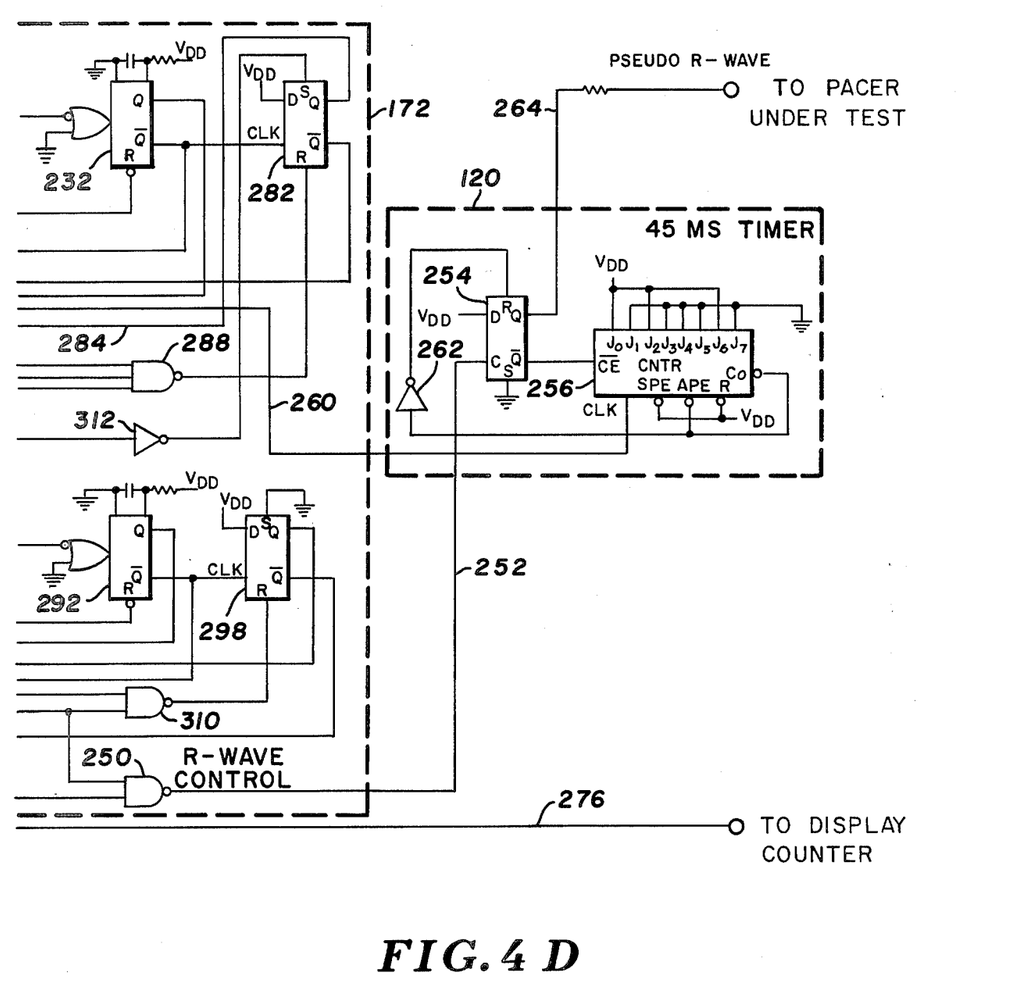

With reference to FIGS. 1 and 3, a demand-type cardiac pacer whose refractory period is to be measured is connected to the test instrument of the present invention such that pacer pulses issued from the pacer pulse generator are applied by way of a line 2 to an Interval Control circuit 4, which circuit is also adapted to receive regularly occurring timing or clock pulse signals by way of line 6. The Interval Control 4 performs two basic functions. First of all, it gates the clock pulses arriving by way of line 6 with the interval between two successive pulses applied by way of line 2. Secondly, it functions to route these gated clock signals to either the A-Interval counter 8 by way of line 10 or the the B-Interval counter 12 by way of line 14. For purposes of explanation only, let it be assumed that the pacer under test is set to operate at 72 bpm which corresponds to a pulse-to-pulse interval to 833 milliseconds. Assuming clock pulses are arriving via line 6 to the Interval Control circuit 4 at a 1 KHz rate, in 833 milliseconds, counter 8 will register the value 833.

Details of the mechanical features of the portable, hand-held, test device in which the present invention may advantageously be incorporated is set forth in the co-pending application of Scott W. Carlson, filed concurrently herewith, and entitled "Midpoint Measuring Circuit". It includes a plurality of push button switches and control knobs for facilitating a number of measurements.

In the second pulse-to-pulse interval following the depression of either the Paced Refractory or Sensed Refractory push button on the instrument's control panel, the Interval Control circuit 4 will route the clock pulses to the B-Interval counter 12 and, assuming that the second interval is identical to the first, the B-Interval counter will also contain a value 833. The generation of the second pacer pulse in a sequence following depression of the keyboard switch labeled "P" which initiates the paced refractory period measurement, causes a so-called Refractory Counter 16 to have a predetermined value entered into it by way of the sequencer logic 18. The value entered into the counter 16 defines the length of the delay following a pacer pulse where the next pseudo R-wave signal is to occur. This value is entered by way of the conductors in cable 20 into a further Downcounter 22 which is arranged to be decremented by a source of clock signals 24. When the interval defined by the countdown of the contents of counter 22 has expired, a signal is generated at an output terminal of the counter 22 and is applied by way of line 24 to a pseudo R-wave Pulse Former circuit 26. This circuit is effective to produce an output signal of a predetermined amplitude and width at the conclusion of the interval defined by the clocking down of the counter 22. This pseudo R-wave is applied to the R-wave sensing amplifier of the cardiac pacer under test and if it occurs outside of the refractory interval of that pacer, it will be effective to reset the pacer's pulse generator and thereby extend the pulse-to-pulse interval.

To determine whether the interval has been extended, the outputs from the A-Interval counter 8 and the B-Interval counter 12 are applied to an Arithmetic Unit 28 which functions to subtract the first interval from the second. The output from the Arithmetic circuit 28 is applied to an Up/Down Control circuit 30 which functions to determine whether the difference so computed is greater than any minimum expected refractory period for pacemaker pulse generators generally.

If the results of the comparison operation indicate that the intervals B and A are substantially identical, i.e., the generation of the pseudo R-wave did not result in an extension, a signal is applied by way of a conductor 32 to the "Up" control terminal of the refractory counter 16. The Sequencer logic 18 then functions to increment the refractory counter by a second predetermined value and the aforementioned sequence of operations is again repeated. If, however, the arithmetic operation performed by circuit 28 reveals that interval B is greater than interval A by a predetermined amount, a control signal will issue on line 34 which connects to the "Down" control terminal of the Refractory Counter 16. When this happens, the value obtained from the Sequencer logic 18 is used to decrease the number contained within the refractory counter 16 and thereby shorten the interval between the occurrence of a pacer pulse and the generation of the next pseudo R-wave by the circuit 26.

It can be seen, then, that the system depicted in the block diagram of FIG. 1 in a series of iterations, seeks out the minimum delay interval at which a pseudo R-wave is just able to effect an extension of the interpulse period of the pacemaker under test.

The Display Control 36 is also coupled to the Up/-Down control 30 by a line 38 which is arranged to carry a signal for advising the display control that the interpulse interval has, in fact, been extended. It also receives a signal from the Sequencer logic 18 by way of a line 40 which indicates that the Refractory Counter 16 is being incremented or decremented in the smallest of several possible amounts, e.g., $+/-10$ ms. When each of these conditions hold true, the Display Control 36 outputs a signal on line 42 which enables a Display Counter 44 such that the contents of the Downcounter 22 may be effectively entered into it. Where, however, the foregoing conditions necessary to produce the enable signal on conductor 42 are not present, a signal is applied by way of line 46 to the Reset terminal of the Display Counter 44 to ready it for the receipt of a new refractory interval value from the Downcounter 22 on a subsequent cycle.

The circuitry thus far described is utilized not only for measuring paced refractory periods but also for measuring sensed refractory periods. In addition, in the latter instance, an additional delay interval is interjected between the occurrence of a pacer pulse and the generation of a subsequent pseudo R-wave. More specifically, and as indicated in the block diagram of FIG. 1, when the system is operating in the sensed refractory mode, the occurrence of a pacer pulse causes a signal to be applied by way of line 48 to the Load terminal of a Downcounter 50. This permits a predetermined digital value, D, to be entered into the counter 50 as a preload condition. Signals from the clock source 24 are then applied by way of line 52 and when the count in the Downcounter 50 reaches zero, it outputs a signal on line 54 for initiating the pseudo R-wave by the Pulse Former 26.

The timing relationship between the pacer pulse generator's output signals and the simulated or pseudo R-wave generated by the test device of the present invention are depicted graphically in FIG. 3 wherein the waveforms A and B relate to the paced refractory measurement and waveforms C and D pertain to the sensed refractory measurement. With no limitation intended, numerical examples are set forth for exemplary purposes.

With reference to waveforms A and B, for purposes of illustration, it is assumed that the pacer pulse generator is issuing pacer pulses at a rate of 72 bpm such that the interval between two successive pulses is 833 milliseconds. During the first phase of operation, interval A is first quantified by counting regularly occurring clock pulses in the A-Interval counter 8 during the period beginning with the leading edge of the first pacer pulse and terminating with the leading edge of the next successive pacer pulse. Next, the Interval Control circuit 4 responds to the second in the series of pacer pulses to cause the clock pulses on line 6 to be entered into the B-Interval counter 12 during the interval defined by the leading edge of the second pulse in the series and the leading edge of the next succeeding (third) pulse. At the same time that the interval B measurement is initiated, a first number from the Sequencer logic 18 is entered into the Downcounter 22 by way of the Refractory Counter 16 and, in the example illustrated by the waveforms A and B in FIG. 3, this value corresponds to a 200 ms delay when counted down by the clock 24. When the contents of the Downcounter 22 reach zero, a pulse is applied by way of line 25 to the pulse former 26 and a pseudo R-wave which may have a pulse width of 45 milliseconds, typically, is generated and applied to the R-wave sensing circuitry of the pacer under test. At the completion of the second interval, i.e., interval $B_1$, the latter interval is compared to the A interval and a determination is made whether the latter interval exceeds the former by a predetermined amount, thereby indicating that the pseudo R-wave was effective to reset the timing circuit of the pacer unit under test. This is the function of the logic circuit 28 in FIG. 1.

In the waveforms A and B of FIG. 3 it is assumed that this first comparison does not indicate a longer B-interval than an A-interval and, as such, the Up/Down control 30 stimulates the "Up" count terminal of the Refractory Counter 16 as the Sequencer logic 18 inserts another increment, for example, a 100 ms increment, into the refractory counter 16. Since it originally contained the initial value of 200 milliseconds, it will now register 300 ms. This value is entered into the Downcounter 22 and it is decremented at a fixed rate by the clock 24. Because of the clock rate chosen, it will reach its all 0's condition in a period of 300 milliseconds and the signal on the line 25 will cause the Pulse Former 26 to issue another pseudo R-wave 300 milliseconds out from the preceding pacer pulse.

While these operations are taking place, the B-Interval counter 12 is again loaded with a value representative of the interval between two successive pacer pulses. The sequence of operations indicated above is continued with additional predetermined time increments being forced into the Refractory Counter 16 by the Sequencer logic 18 until such time that the Arithmetic circuit 28 detects an extension of the B-interval. At this point, the Up/down countrol circuit 30 will output a control signal on line 34 to stimulate the Down control terminal of the Refractory Counter 16. Hence, the next increment from the Sequencer logic will be subtracted from the interval registered in the Refractory Counter 16 and, as a result, the point at which the pseudo R-wave is generated will be shifted so as to become generally aligned with the point marking the end of the pacer pulse generator's refractory period. The Display Control circuitry 36 senses when the Sequencer 18 is issuing predetermined short increments to the Refractory Counter 16 and when an interval extension occurs as reflected by the output of the Up/Down control circuit 30. The Display Control 36 then enables the Display Counter 44 by way of a signal on line 42 such that the interval previously registered in the Downcounter 22 representing the displacement between the leading edge of a pacer pulse and the termination of the refractory interval. This number is then presented on the display readout device (not shown) so as to indicate to the user the refractory interval of the pacer under test.

Waveforms C and D of FIG. 3 illustrate the system operation when sensed refractory intervals are being measured. As was indicated earlier, a sensed refractory interval is that time period following a sensed electrical signal which is picked up by heart contacting electrodes and detected by a pulse generator during which the pulse generator's sensing circuit is unresponsive to further electrical signals which may be picked up by those electrodes. That is, during the sensed refractory interval, further electrical impulses are incapable of resetting the timer circuit of the pacer pulse generator.

In measuring the sensed refractory interval, the question to be resolved may be expressed as, "How long after the pulse generator has sensed an R-wave must it wait before it can sense another R-wave?". As such, the test circuit of the present invention is designed to measure a reference interval including an R-wave that is known to be outside of the refractory period of the various pacer pulse generators on the market. In that the normal refractory period for a pacer may, for example, be about 350 milliseconds, if a delay of 600 milliseconds is created between the occurrence of a pacer pulse and the generation of a first pseudo R-wave, it is a certainty that the R-wave occurred outside of the refractory period for the pacer.

Again if it is assumed that the pacer under test is operating at 72 bpm, such that it has a normal pulse-to-pulse interval of 833 milliseconds, the interval between pulses illustrated in waveform C will be $833 + 600 = 1433$ milliseconds in that the first simulated or pseudo R-wave occuring 600 milliseconds following the first pulse will be effective to reset the pulse generator's timing circuit, causing it to begin anew to charge up a capacitor in an R-C timing arrangement or to accumulate pulses in a digital counter until the 833 millisecond time interval has elapsed. At this point, then, which is 1433 milliseconds from the original pulse, the pacer will be effective to generate a second pacer pulse. Thus, during the initial interval, the A-Interval counter 8 will accumulate a number of pulses from the clock source connected to line 6 so as to reflect a 1433 ms time interval. At this point, i.e., at the occurrence of the second pacer output pulse, the Interval Control 4 takes over to begin loading the B-Interval counter 12. At the same time, the counter 50 is again loaded with the 600 ms count and when this period has elapsed, the Pulse Former 26 issues a pseudo R-wave. At the conclusion of the 600 millisecond time interval, the delay circuit 50 outputs a signal on line 54 which is applied as an enable signal to the Downcounter 22, via line 56. The Sequencer 18 has already loaded the Refractory Counter 16 with a first increment, e.g., 200 milliseconds, and, as such, upon the occurence of the enable signal on line 56, this value is transferred, via lines 20, into the Downcounter 22. When th Downcounter 22 is decremented to zero, it outputs a signal on the line 24 for again initiating the Pulse Former circuit 26, thereby issuing a second pseudo R-wave 200 milliseconds following the occurence of the first pseudo R-wave.

The foregoing action continues with the exception that during subsequent cycles, the time between the initiation of the first pseudo R-wave of a set and the occurrence of the second is adjusted in incremental steps under control of the Sequencer 18.

Ultimately, a point is reached where the Display Control circuit 36 senses that an extension of the B-interval has occurred and that the Sequencer 18 is adjusting the refractory interval in predetermined minimum increments, e.g., +/−10 ms. At this time, the Display Counter 44 is enabled to receive the interval measurement from the Downcounter 22. Once the information is contained within the Display Counter, it becomes available to the LED display panel for visual presentation to the user.

Figure 2:
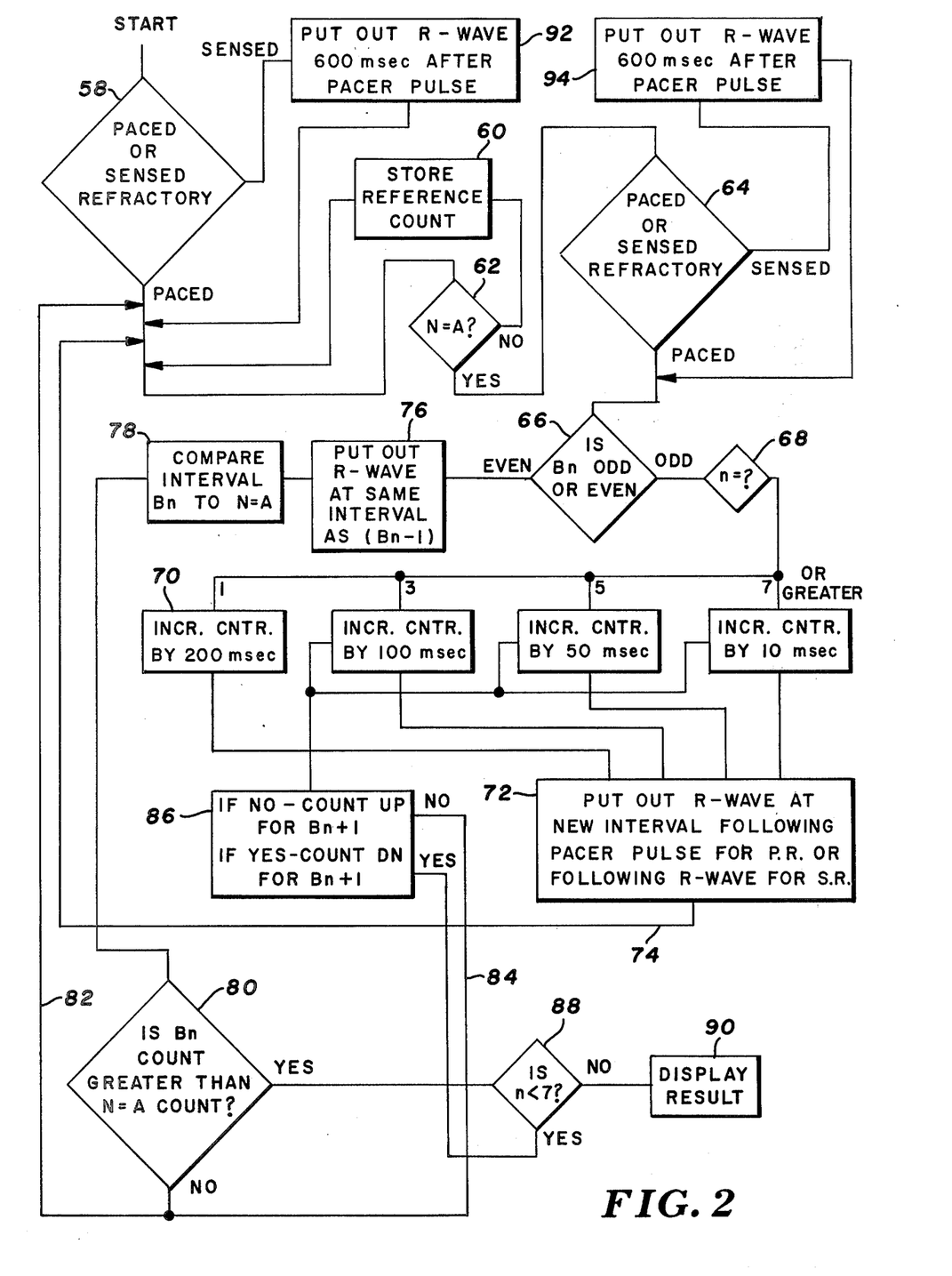
FIG. 2 is a flow diagram helpful in explaining the mode of operation of the present invention.

FIG. 2 presents a flow diagram which is a still further aid in understanding the overall sequence of events occurring within the refractory interval measuring circuitry of the present invention. When either the "Paced" push button switch, P, on the keyboard or the "Sensed" push btton, S, is depressed (see FIG. 1), the measurement process is initiated and in the decision block 58, it is determined whether a sensed refractory or a paced refractory interval is to be measured. Assuming it is the paced interval, a further test is made to determine whether a complete pulse-to-pulse interval has been entered into the A-Interval counter 8. If not, the operation represented by block 60 is performed and, again, a test is made in block 62 to ensure that a value corresponding to a complete pulse-to-pulse interval has, in fact, been entered into the A-Interval counter 8.

In that the assumption has already been made that it is a paced refractory period being measured, the path out of the bottom of the decision block 64 is followed and a further test is made to determine whether the B-interval being measured is odd or even. That is, on the first iterative cycle, n will be odd (1 is an odd number) and an exit is made to the right from the decision block 66. On a next succeeding cycle, i.e., the second iterative cycle, n will equal 2, which is even, and the exit from decision block 66 will be from its bottom.

Backing up momentarily, then, considering the first iteration where n is odd, in decision block 68 a determination is made whether n=1, 3, 5, 7 . . . . Because the assumption is made that it is the first iterative cycle which is under consideration, n will equal 1 and, as a result, the sequencer logic 18 will enter a 200 millisecond increment into the Refractory Counter 16 of FIG. 1. This operation is represented by box 70 in the flow diagram of FIG. 2.

By continuing to trace through the flow diagram of FIG. 2, it can be seen that the next operation is represented by box 72 which indicates that the circuitry is to put out an R-wave at a new interval following a pacer pulse when operating in the paced refractory measurement mode or following an R-wave when operating in the sensed refractory measurement mode. Because the initial assumption was made that the device is measuring a paced refractory interval, the pseudo R-wave will be produced 200 milliseconds following the occurrence of a pacer pulse.

Following line 74, it can be seen that the flow diagram is reentered between decision blocks 58 and 62 and again, one can trace through the flow diagram to the decision block 66. Here it will be determined that since it is the second iteration which is under consideration n is even and an R-wave is produced at the same interval from a preceding pacer pulse as in the prior iteration, i.e., 200 milliseconds following the pacer pulse. This operation is represented by block 76.

Next, interval $B_n$ is compared to interval A (box 78) and a decision is made at 80 as to whether the B-interval has been extended. Assuming that it has not, the path exits from the bottom of the decision block 80 and follows line 82 back to the re-entry point above decision block 62. Also, if no extension is sensed at block 80, one may follow the path 84 to operation block 86 which indicates that when no extension has taken place, the next incrementation of the refractory counter by the sequencer logic is to cause the counter 16 to be advanced by the specified increment. The foregoing operation continues on an iterative basis whereby on odd cycles, the point at which the pseudo R-wave is issued relative to the occurrence of a pacer pulse is changed in prescribed steps, e.g., 200, 100, 50 and 10 milliseconds, until it is determined in decision block 80 that interval B is greater than interval A. When this first happens, the flow path exits to the right from decision box 80 and a new decision is made whether fewer than seven iterations have taken place (box 88). If so, the path to be followed is from the bottom of decision block 88 to the block 86 which specifies that the next increment to be applied by the Sequencer to the Refractory Counter 16 is in a downward or decreasing direction.

When n is seven or greater, the flow is to the right from the decision block 88 which indicates by operation block 90 that the interval now present in Refractory Counter 16 may be displayed.

With the foregoing explanation of the flow diagram in mind, it is felt to be readily apparent how the system operates when measuring sensed refractory periods. Here, the only significant change is represented by the operation blocks 92 and 94, which indicates that a R-wave is to be issued 600 milliseconds following a pacer pulse, and in operation block 72, that a further R-wave is to be produced at the prescribed interval following that first R-wave as determined by the contents of the Refractory Counter 16.

Now that the details of the overall operation are in mind, consideration will be given to the specifics of an exemplary embodiment whereby the system depicted diagrammatically in FIG. 1 may be realized with known digital logic devices. In this regard, reference is made to the logic diagram of FIGS. 4A through 4D.

For convenience, the detailed logic diagram has been partitioned by a series of dashed line boxes which have been labeled to show the correspondence between the circuitry contained therein and the functional block diagram of FIG. 1. For example, dashed line box 100 labeled "Interval Control" includes those circuits used to control the loading of interval information into the A-interval counter and the $B_n$-interval counter at the appropriate times relative to the occurrence of output pulses by the pacer under test. Similarly, the dashed line box identified by numeral 102 comprises the $B_n$-Interval counter and that inclosed by dashed line box 104 comprises the integrated circuits forming the A-Interval counter. The Arithmetic circuitry used to determine whether the $B_n$ interval has been extended due to the generation of a pseudo R-wave pulse outside of the refractory interval is shown as being enclosed by the dashed line box 106. The Sequencer logic surrounded by dashed line box 108 controls the size and time of occurrence of an incrementing value to be inserted into the Refractory Counter. The Refractory Counter, itself, is shown as being enclosed by dashed line box 110. The circuitry used to control whether the Refractory Counter will be incremented or decremented by the value supplied by the Sequencer logic is the Up/Down control, shown surrounded by dashed line box 112. The circuits surrounded by the dashed line box 114 control the entry of a value into the Display Counter corresponding to the ultimately determined refractory interval.

The circuits corresponding to the Downcounter 22 in the block diagram of FIG. 1 are shown as being enclosed by the broken line box 116 and the 600 millisecond Delay network is surrounded by broken line box 118. The 45 millisecond Timer basically includes those circuits enclosed by dashed line box 120, while the Control circuit for ensuring that the R-wave is generated at a predetermined delay when in the sensed refractory mode is shown as enclosed by broken line box 122.

Referring first to the Interval Control circuits, a depression of either the Paced Refractory push button or the Sensed Refractory push button on the operator's control panel causes the NOR gate 130 to output a signal which is connected by a conductor 132 to the reset terminals of a D-type flip-flop 134 and to the BCD (binary coded decimal) Up-counter comprised of cascaded integrated circuits 136 and 138. It is thus readied to receive clock pulses which quantify the interpulse interval of the pacer under test. In this regard, line 140 is adapted to be coupled to the pacer under test and carries a high signal during even pulse-to-pulse periods and a low signal during odd pulse-to-pulse periods. Thus, during the first interval, the signal on line 140 will be low, partially enabling the NOR gate 142 and disabling NOR gate 144 by way of the signal output from inverter 146. With NOR gate 142 partially enabled, 100 Hz clock signals from a source of clock pulses (not shown) are applied by way of conductors 148 and 150 to the NOR gate 142 which are then propagated through NAND gate 152 which, at this time, is partially enabled by the now reset flip-flop 134. The clock signals thus enter the A-Interval counter chip 136 causing it to be advanced, so long as the signal on conductor 140 remains low. At the conclusion of the interpulse interval, however, the signal on line 140 goes high, clocking the flip-flop 134 to its set state and disabling the NAND gate 152. Because the signal on line 140 is now high, inverter 146 will output a low signal to NOR gate 144 whose output is connected by way of a conductor 154 to the clock input terminal of the $B_n$-Interval counter, including the Presettable Downcounter chip 156 which is cascaded to a further BCD counter 158. Thus, so long as the signal on line 140 remains high during the B-Interval, clock pulses will propagate through the NOR gate 144 to advance the counter.

Backing up for a moment, at the conclusion of the first interpulse period, a signal is applied to the line 160 which causes the inverter 162 to output a high signal which is applied to the Preload Enable terminal (PE) of the counter circuit 156 and to the reset terminal of the counter chip 158. As such, the counter is preloaded with the digital value, 20. Thus, the count developed within the $B_n$-Interval counter corresponds to the actual length of the $B_n$-Interval plus a bias of 20 counts.

The value corresponding to the A-interval stored in the integrated circuits 136 and 138 is applied in parallel to the inputs of a 9's Complementer comprised of integrated circuit chips 164 and 166. The controls on this circuit are such that the signals appearing at its output terminals $F_1$ through $F_4$ comprise the 9's complement of the A-value. These signals are, in turn, tied directly to corresponding inputs of a natural binary coded decimal (NBCD) adder circuit comprised of the integrated circuits 168 and 170. Formed in the NBCD adder, then, is the quantity $B_n+20+(-A)$. The most significant digit of the result ends up in the adder chip 170 whereas the least significant digit will reside in the chip 168. The outputs from the adder are applied individually to inputs of a NOR gate 172. As such, if any of these outputs is a binary 1 signal, NOR gate 172 will output a low signal, indicating that the $B_n$-interval has been extended. A binary "1" at the output of NOR gate 172 indicates that the pseudo R-wave was ineffective to extend the interval in question.

The output from NOR gate 172 is coupled through an inverter 174 to a first input of a NAND gate 176. If no extension has taken place, gate 176 will output a binary 1 signal which is inverted by circuit 178 and applied to the D-input terminal of the Up/Down Control flip-flop 180. On the next arriving pacer pulse, line 182 goes low and, as a result, the flip-flop 180 remains in the same state, i.e., reset. The $\overline{Q}$ output from the flip-flop 180 is applied by way of a conductor 184 to the Up/Down control terminal of the Refractory Counter comprised of presettable up/down counter integrated circuit chips 186 and 188. On the other hand, if the NOR gate 172 had outputted a binary "0" signal, indicating that the $B_n$-Interval had been extended, inverter 178 would ultimately output a binary "1" signal. As such, on the next pacer pulse received, the flip-flop 180 would be clocked to its set state, resulting in a reversal of the state of the signal applied to the U/D input control terminals of the counter chips 186 and 188. As is well known in the art, whether the contents of the counter comprised of the chips 186 and 188 will be incremented or decremented is determined by the state of the signal (binary 1 or binary 0) applied to that terminal.

The value itself to be entered into the counter comprised of the chips 186 and 188 is determined principally by the Sequencer logic enclosed by dashed line box 108. As is reflected in the flow diagram of FIG. 2, changes can take place only during odd iterations and during even iterations of the Sequencer, the contents of the Refractory Counter remain unchanged. It is during the even iterations that the comparison operations are completed, and the new values are entered into the appropriate counters. Furthermore, during the first iteration, a predetermined count such as 200 milliseconds is entered. Subsequently, during a third iteration, an additional count of 100 milliseconds is entered into the Refractory Counter leaving a total of 300. During the fifth iteration, an additional 50 millisecond value is added (or subtracted) and during the seventh and subsequent odd iterations, the count contained in the Refractory Counter 110 is either increased or decreased by a value corresponding to 10 milliseconds. The manner in which this is accomplished will now be set out.

When either the paced refractory or sensed refractory push button on the keyboard is depressed, NOR circuit 130 outputs a signal on the line 132 which is also applied by way of lines 190 and 192 to the reset terminals of a pair of flip-flops 194 and 196. This same signal also resets the Refractory Counter chips 186 and 188 by way of the signal on lines 192 and 198. With both flip-flops 194 and 196 reset, their respective Q output terminals will be low, thereby presenting a 0,0 pattern to the A and B inputs of the Multiplexer/Demultiplexer chip 200. This action establishes an internal connection between the $X_0$ input of the device 200 to the X output thereof. Keeping this in mind, then, it is to be noted that regularly occurring clock signals, for example, a 600 KHz signal, is applied by way of a line 202 to the clock input of a decade counter device 204. When this counter receives ten input pulses, an output results on line 206 which connects to the clock input terminal of a toggle flip-flop 208. The $\overline{Q}$ of flip-flop 208 is, in turn, connected to the clock input of a further flip-flop 210 whose Q output connects to the $X_0$ input of the Mux/Demux device 200. It can be seen, then, that the X output will remain low until a time equivalent to 20 clock pulses has transpired. During this interval, the NAND gate 214 is enabled, causing it to output a low signal which is inverted at 216, causing NAND gate 218 to be partially enabled. The clock pulses on line 202 are coupled by way of conductor 220 to a second input of NAND gate 218 and, hence, now pass through it and the NAND gate 222 to the clock input of the Refractory Counter 186/188. After the 20th pulse, X output goes high for a fraction of one clock cycle, which in turn, disables NAND gate 214 and also disables NAND gate 218 via Inverter 216. In that the same clock source that controls the Multiplexer/Demultiplexer 200 is also used to advance the counter 186/188, a count of 20 will be inserted into the refracted counter. This corresponds to an initial time interval of 200 milliseconds.

This quantity becomes available at the $Q_1$-$Q_4$ outputs of the chips 186 and 188 and is applied to the jam inputs of the Downcounter 224. The count corresponding to the 200 millisecond interval will be entered into the Downcounter 224 when its Asynchronous Preload Enable terminal (APE) is stimulated. Upon the occurrence of each pacer pulse received by the test instrument, a signal on the conductor 226 goes low which, in turn, triggers a one-shot circuit 228 causing a high signal to be applied temporarily to the conductor 230. The conductor 230, in turn, leads to a further one-shot circuit 232 which becomes triggered by the trailing edge of the signal on line 230. This action generates the APE signal needed to effect loading of the Downcounter 224. Once this value is contained in the counter, it is arranged to be counted down by 100 Hz clock pulses emanating from the BCD counter 234. As the count in the Downcounter 224 is decremented, a point is reached where its contents are reduced to zero and a carry output (C.O.) appears on conductors 236 and 238 connected to the clock input of a toggle flip-flop 240. This causes the toggle flip-flop 240 to revert to its opposite state and a low signal is applied by way of conductor 242 to an input of NAND gate 244. Being a low signal, NAND gate 244 outputs a high signal which switches the flip-flop 194 to its opposite state. As a net result, a binary pattern 1,0 is applied to the A and B inputs of the Mux/Demux device 200. With this pattern applied, the input terminal $X_1$ will be internally connected to its X output. This time, the NAND gate 218 will be held open sufficiently long to permit only ten clock pulses to be applied to the refractory counter chips 186/188. This corresponds to an incrementation of 100 milliseconds.

On subsequent cycles, the flip-flops 194 and 196 are switched so as to present, in sequence, the patterns 0,1 and 1,1 to the A and B inputs of the Multiplexer/Demultiplexer 200. When it is the pattern 0,1 that is applied, stage $Q_5$ of the decade counter 204 is coupled through the multiplexer such that five clock pulses are capable of passing through the gate 218 to the clock input of the Refractory Counter, corresponding to an increment of 50 milliseconds. Finally, when the 1,1 pattern is applied to the A, B inputs of device 200, the NAND gate 222 will be enabled for only a single clock period such that the refractory counter will be incremented or decremented by 10 milliseconds.

Each time the Mux/Demux 200 outputs a logic signal, it is applied to the clock input of a further flip-flop 246 which, in turn, controls the display circuitry in a manner yet to be described.

The output signals from the device 200 are also connected so as to reset flip-flops 208 and 210 and the counter 204. As such, these circuits are conditioned and ready to carry out a subsequent cycle.

Summarizing momentarily, it has been shown the manner in which the A and B-interval values may be loaded into the counters 156/158 and 136/138 and how those values are compared to determine whether there has been a interval extension occasioned by the occurrence of a pseudo R-wave pulse. The manner in which successively different time increments may be introduced into the Refractory Counter 186/188 under control of the Sequencer has also been explained. Furthermore, the details of the circuits used to govern whether the sequentially introduced increments will add to or detract from the interval developed within the Refractory Counter has been set out. Attention will next be directed to the manner in which the pseudo R-wave signals are developed, and that will be followed by an explanation of the manner in which a predetermined 600 millisecond delay interval is introduced into the cycle of events when sensed refractory periods are being measured.

As was earlier pointed out, when the values contained within the Downcounter 224 are decremented to zero by the 100 Hz clock pulses, a low signal appears on conductor 236 and is applied to NAND gate 250 which then outputs a high signal on line 252 and which clocks the flip-flop 254 to its set state. With flip-flop 254 in its set state, a pseudo R-wave signal is applied by way of conductor 264 to the pacer under test. A high signal on 252 also applies a clock enable signal to a presettable BCD downcounter 256 which is hard wired to receive a value equal to 45 each time the Asynchronous Preload Enable input thereto is stimulated. Assuming that a count of 45 is contained in the device 256, the 1 KHz clock signals applied to it by way of conductors 258 and 260 will result in a low signal at the carry overflow (C.O.) terminal 45 milliseconds following the switching of the flip-flop 254. This signal performs a number of functions. This results in a reloading of the counter 256 with a count of 45, it resets the flip-flop 254 by way of the output from an inverter 262 and ultimately causes the pseudo R-wave signal applied by way of conductor 264 to the pacer under test to be terminated.

From the immediately foregoing explanation, it can be seen that following the expiration of the time interval entered into the downcounter 224, the circuitry enclosed by the dashed line box 120 causes a impulse having a pulse width of 45 milliseconds to be applied as a pseudo R-wave to the pacer unit under test. This R-wave may then result in a resetting of the pulse generator's timing circuit if it occurs outside of the refractory interval established for that pacer device. If not, the test circuitry of the present invention operates to further extend the delay period from the occurrence of a pacer pulse to the generation of a pseudo R-wave in predetermined steps until extension is noted. Following that, the interval is decremented in small discrete steps of 10 milliseconds each until no extension is detected. Next, the interval is increased by 10 milliseconds and the circuitry shows that an extension has taken place. At that point, it is known that the interval developed within the Refractory Counter and Downcounter corresponds very closely to the refractory interval for the pacer under test. As such, it is desired to display that reading. The manner in which the display is energized will now be set forth.

Referring again to FIG. 4B, it was indicated that the inverter 178 outputs a signal to the Up/Down control flip-flop 180 when the NOR gate 172 senses an extension of the $B_n$-Interval beyond its original length. This signal is also applied to the clock input terminal of a flip-flop 266 associated with the display control function. This flip-flop, as well as the associated flip-flop 268, is held in a reset state by the output from the flip-flop 246 via conductor 270 and, as such, the output from the inverter 178 is ineffective to alter the states of the flip-flop 266 and 268 until the reset is released. The flip-flop 246 is arranged to be clocked to its reset state only when the refractory counter 186/188 is being incremented or decremented in steps of 10. This is the function of the NAND gate 270. When the aforementioned condition is satisfied, both inputs to NAND gate 270 will be high and it will output a low signal to the D-input of the flip-flop 246. Then, upon the next output from the multiplexer 200, flip-flop 246 will be clocked so as to release the reset on the display control flip-flops 266 and 268. With flip-flop 268 in its set condition, a high signal is applied by way of the conductor 272 to the clock enable terminal (C.E.) of the Refractory Counter chip 186. This action precludes the contents of the refractory counter from being altered until released and also generates a high signal on conductor 274 which connects to the Display Counter (not shown) thereby enabling it to display a value corresponding to the interval then contained within the refractory counter. The value actually entered into this display counter comes from the output of the counter 234 on the conductor 276. As was already mentioned, counter 234 functions to release a number of 100 Hz clock signals. The details of the construction of a display counter and LED decoding and driving circuitry as well as a LED display panel itself suitable for use herein is set out in the copending application of James T. Bartelt, filed concurrently herewith, and entitled Cardiac Pacer Testing System.

As has already been explained, each pacer pulse received by the test instrument of the present invention triggers the one-shot 228, causing it to output a signal on the line 230 which, in turn, triggers the one-shot circuit 232 to reset the counter 234. When the state of flip-flop 134 changes to permit the entry of the A-interval into the counters 136 and 138, a low signal appears on the Q output of the flip-flop 134 and this signal is applied by way of conductors 278 and 280 to the clear terminal of the Downcounter 224, and to the reset terminal of the one-shot circuit 232. This signal initializes these two devices. Now, at the conclusion of the A-interval, one-shot circuit 228 is triggered causing the signal on line 230 to go low momentarily to trigger the one-shot circuit 232. When this happens, the $\overline{Q}$ side of 232 goes low for a short time to allow the count from the Refractory Counter 110 to be loaded into the counter 234. When the $\overline{Q}$ output of the one-shot circuit 232 returns to a high, flip-flop 282 is clocked to provide the signal on line 284 for enabling clock pulses from the 1KHz source (not shown) to drive the counter circuit 234. This circuit effectively divides the clock rate by 10 such that 100 Hz signals appear on the conductor 276 and pass through the inverter 286 to decrement the Downcounter which had previously been loaded with the value from the Refractory Counter 186/188. As soon as the number of pulses needed to decrement that counter to zero have arrived, a low signal is applied by way of conductor 236 and the NAND gate 288 to the reset terminal of the flip-flop 282. Resetting of this flip-flop blocks the passage of any further clock pulses through the counter 234 by virtue of the signal on line 284. Hence, the number of pulses in the burst appearing on conductor 276 is a measure of the refractory interval of the pacer under test.

The operation of the system has been described above in connection with the measurement of paced refractory intervals. Consideration will now be given to the minor modifications which are made to the circuitry in order to permit measurement of sensed refractory intervals.

The depression of the push button switch on the panel of the test instrument to initiate a sensed refractory interval measurement causes a signal to appear on conductor 290 which releases the reset on a one-shot circuit 292. The $\overline{Q}$ output of this flip-flop is connected to the asynchronous preload enable terminal (APE) of a Presettable Downcounter 294 by a conductor 296 and, as a result, a predetermined number programmed into its jam inputs is entered into the counter 294. This predetermined number is the binary coded decimal equivalent of the value 60. The $\overline{Q}$ output from the flip-flop 292 also clocks a flip-flop 298 which causes a Clock Enable to be applied to a decade counter 300 by way of conductor 302 and to the BCD Presettable Downcounter 294 by way of conductor 304. The 1 KHz clock signals on line 258 are applied to the counter 300 and this clock rate is effectively divided by 10 by virtue of the output obtained from stage $Q_4$ thereof. These 100 Hz clock signals are inverted at 306 and used to count down the downcounter 294. After 60/100 seconds or 600 ms, the counter 294 outputs a C.O. signal on line 308 to thereby reset the flip-flop 298 via NAND gate 310 and to clock the flip-flop 254 by way of the output from NAND gate 250. The carry output from the Downcounter 294 also passes by way of an inverter 312 to the set terminal of the flip-flop 282 which, as mentioned previously, controls the enabling of the transmission of clock pulses to the downcounter 224.

By carefully tracing the above-described logic circuits, it will be observed that the 600 ms delay will be inserted between the leading edge of a first pacer pulse and the leading edge of a first pseudo R-wave. Then, a predetermined time later determined by the Sequencer logic, a second pseudo R-wave impulse is generated, all as depicted in the waveforms C and D of FIG. 3.

For purposes of illustration, and with no limitation intended, there is set forth in the table an indication of commercially available integrated circuit devices which may be used in constructing the illustrative embodiment.

| DEVICE | TYPE |
| --- | --- |
| Counter 156, 186, 188 | 4510 B |

-continued

| DEVICE | TYPE |
| --- | --- |
| Counter 158, 136, 138, 234, 300 | 4518 B |
| Counter 256, 224, 294 | 40102 B |
| D-flip-flops (all) | 4013 B |
| Counter 204 | 4017 B |
| NOR gates (all) | 4001 B |
| 9's Complementor | 14561 B |
| NBCD Counter | 14560 B |
| Inverters (all) | 4069 B |
| One-shot 228 | 14538 B |
| 8-Input NOR Gate | 4078 B |
| NAND Gates | 4011 B or 4023 B |
| Multiplexer 200 | 4052 B |
| One-shots 232, 292 | 4098 B |

The invention has been described in considerable detail with respect to a particular implementation thereof as reflected in the drawings. However, those skilled in the art of digital logic design will conceive of alternative configurations which may be used to perform substantially the same function in substantially the same way. Hence, the invention is not to be limited to the particular configuration depicted, but its scope should be determined from the following claims.

What is claimed is:

1. A method for measuring the refractory period of a demand-type cardiac pacer pulse generator comprising the steps of:
   (a) measuring a first interval between successive output pulses from said pulse generator;
   (b) applying a pseudo R-wave to said cardiac pacer at a first predetermined time following the occurrence of a pacer pulse generator output pulse;
   (c) measuring an additional interval between successive output pulses from said pulse generator following the occurrence of said pseudo R-wave;
   (d) comparing said first interval measurement to said additional interval measurement to determine if said additional interval is greater than said first interval;
   (e) adjusting the time of application of said pseudo R-wave to said cardiac pacer relative to pacer output pulses in predetermined increments depending upon the results of said comparing step; and
   (f) repeating steps (b) through (e) until said additional interval is greater than said first interval after a predetermined number of iterations.

2. The method as in claim 1 and further including the steps of:
   (a) measuring the period between a pacer output pulse and the occurrence of said pseudo R-wave at a time following said predetermined number of iterations; and
   (b) presenting a visual readout of the length of said period.

3. The method as in claim 1 wherein step (e) comprises:
   (a) increasing the time period between said pacer output pulses and said pseudo R-wave in predetermined steps until said additional interval exceeds said first interval;
   (b) decreasing the time period between said pacer output pulses and said pseudo R-wave in predetermined steps of lesser magnitude until said additional interval no longer exceeds said first interval;
   (c) again increasing the time period between said pacer output pulses and said pseudo R-waves in predetermined steps of still lesser magnitude until said additional interval exceeds the said first interval; and
   (d) repeating steps (b) and (c) where the predetermined steps on each iteration are of a lesser magnitude until the said additional interval again exceeds the said first interval and the steps are of the smallest predetermined magnitude employed.

4. A method for measuring the sensed refractory period of a demand-type cardiac pacer pulse generator in a predetermined number of iterative cycles comprising the steps of:
   (a) initiating a first reference interval upon the detection of a first pacer output pulse;
   (b) applying a first pseudo R-wave a predetermined time following said first pacer pulse, said time being greater than the paced refractory interval of pacer pulse generators to be tested;
   (c) terminating said first reference interval upon the detection of the next pacer output pulse following said first pacer output pulse;
   (d) measuring said first reference interval;
   (e) applying a second pseudo R-wave to said pacer pulse generator said predetermined time following said next pacer output pulse;
   (f) applying a third pseudo R-wave to said pacer pulse generator at a known interval following the application of said second pseudo R-wave to said pacer pulse generator;
   (g) measuring a subsequent interval between adjacent pacer pulse generator output pulses following the occurrence of said third pseudo R-wave;
   (h) determining whether said subsequent interval exceeds said first reference interval;
   (i) adjusting the time of application of said third pseudo R-wave to said pacer pulse generator relative to said second pseudo R-wave in predetermined increments depending upon the results of step (h); and
   (j) repeating steps (e) through (i) until said subsequent interval is greater than said reference interval following said predetermined number of iterative cycles.

5. The method as in claim 4 and further including the steps of:
   (a) measuring the interval between said second and said third pseudo R-waves when said subsequent interval exceeds said reference interval at the conclusion of said predetermined number of iterative cycles; and
   (b) presenting a visual display of the interval measured in step (a).

6. The method as in claim 4 wherein step (i) comprises:
   (a) increasing the time period between said second pseudo R-wave and said third pseudo R-wave in predetermined increments until said subsequent interval exceeds said reference interval; and
   (b) decreasing the time period between said second pseudo R-wave and said third pseudo R-wave in predetermined increments of lesser magnitude until said subsequent interval no longer exceeds said reference interval;
   (c) again increasing the time period between said pacer output pulses and said pseudo R-waves in predetermined steps of still lesser magnitude until said additional interval exceeds the said first interval; and (d) repeatng steps (b) and (c) where the predetermined steps on each iteration are of a lesser magnitude until the said additional interval again exceeds the said first interval and the steps are of the smallest predetermined magnitude employed.

7. Apparatus for measuring the duration of the refractory period of a demand cardiac pacer of the type which normally generates pacer pulses of a predetermined frequency in the absence of naturally occurring R-wave signals from the heart, comprising:
  (a) first measuring means for measuring the interval between successive pulses of the pacer being tested;
  (b) pulse producing means for applying pseudo R-waves to the pacer being tested;
  (c) second measuring means for measuring the interval between successive pulses following the application of said pseudo R-wave to said pacer being tested;
  (d) comparison means coupled to said first and second measuring means for determining if said interval measured by said second measuring means is greater than the interval measured by said first measuring means;
  (e) an up/down counter;
  (f) sequencer means coupled to said up/down counter for altering the contents of said up/down counter in predetermined steps, the direction of said steps being controlled by said comparison means;
  (g) means coupling said up/down counter to said pulse producing means for generating said pseudo R-waves at intervals determined by the contents of said up/down counter; and
  (h) display means coupled to said comparison means for presenting a visual indication of the contents of said up/down counter following a predetermined number of said steps.

8. Apparatus for measuring the length of the refractory period of a cardiac pacer, comprising:
  (a) a first digital counter;
  (b) a second digital counter;
  (c) a source of regularly occurring clock signals;
  (d) control means connected to receive said regularly occurring clock signals, said control means receiving pacer pulses from said cardiac pacer under test and connected to said first and second digital counters for routing said clock signals to said first digital counter during a first interpulse interval and to said second digital counter during subsequent interpulse intervals;
  (e) arithmetic means for subtracting the contents of said first digital counter from the contents of said second counter;
  (f) detector means coupled to said arithmetic means for indicating whether the difference formed by said arithmetic means is greater than or less than a predetermined value;
  (g) an up/down counter having an up/down count control terminal connected to receive control signals from said detector means;
  (h) sequencer means operative on successive iterative cycles for entering predetermined increments into said up/down counter; and
  (i) pulse former means coupled to said up/down counter for producing a first pseudo R-wave pulse at a time interval following the occurrence of said pacer pulses determined by the contents of said up/down counter.

9. The apparatus as in claim 8 and further including:
  (a) timer means adapted to be initiated by the occurrence of said pacer pulses;
  (b) means connecting said timer to said pulse former means for producing a second pseudo R-wave signal at a predetermined time following the occurrence of said pacer pulses, said first pseudo R-wave pulse occurring at a time following the occurrence of said first pseudo R-wave pulse determined by the contents of said up/down counter.

* * * * *